United States Patent [19]

Pudlo

[11] Patent Number: 5,618,279
[45] Date of Patent: Apr. 8, 1997

[54] MEDICAL PROTECTION DEVICE FOR MALES

[75] Inventor: Edward S. Pudlo, 3956 Ruppel Rd., Port Hope, Mich. 48468

[73] Assignee: Edward S. Pudlo, Port Hope, Mich.

[21] Appl. No.: 345,019

[22] Filed: Nov. 23, 1994

Related U.S. Application Data

[63] Continuation of Ser. No. 63,939, May 19, 1993, abandoned.

[51] Int. Cl.$^6$ ............................... A61F 5/44; A61F 13/15
[52] U.S. Cl. ..................... 604/385.1; 604/347; 604/349; 2/403
[58] Field of Search ................... 602/67–73; 128/98.1; 2/403, 405; 604/317, 327, 346–353, 355–358, 385.1, 385.2, 386, 387, 393–396

[56] References Cited

U.S. PATENT DOCUMENTS

| | | | |
|---|---|---|---|
| 208,240 | 9/1878 | Hill | 602/71 |
| 741,173 | 10/1903 | Seidel . | |
| 1,228,452 | 6/1917 | Lawrence | 604/353 |
| 1,490,793 | 4/1924 | Ajamian et al. | 604/353 |
| 2,038,242 | 4/1936 | Schwartz | 602/67 |
| 2,138,626 | 11/1938 | Copen . | |
| 2,222,825 | 11/1940 | Starck . | |
| 2,445,694 | 7/1948 | Predmore . | |
| 2,591,783 | 4/1952 | Craddock . | |
| 2,842,129 | 7/1958 | Ernstorff | 604/396 |
| 2,864,369 | 12/1958 | Morrow . | |
| 2,920,625 | 1/1960 | Green | 604/348 |
| 3,035,579 | 5/1962 | Benovic . | |
| 3,067,336 | 12/1962 | Eachus . | |
| 3,161,198 | 12/1964 | Moxley | 604/353 |
| 3,397,698 | 8/1968 | Hickey | 604/353 |
| 3,526,227 | 9/1970 | Appelbaum . | |
| 3,536,066 | 10/1970 | Ludwig . | |
| 3,547,117 | 12/1970 | Smithers . | |
| 3,707,969 | 1/1973 | Sanford . | |
| 3,882,859 | 5/1975 | Ericson . | |
| 4,197,849 | 4/1980 | Bostick | 604/352 |
| 4,378,010 | 3/1983 | McDonald | 602/70 |
| 4,381,782 | 5/1983 | Mazurak et al. . | |
| 4,387,726 | 6/1983 | Denard | 604/353 |
| 4,417,146 | 11/1983 | Herbert . | |
| 4,423,523 | 1/1984 | Bodner et al. . | |
| 4,427,408 | 1/1984 | Karami et al. | 604/393 |
| 4,453,938 | 6/1984 | Brendling . | |
| 4,553,968 | 11/1985 | Komis . | |
| 4,568,340 | 2/1986 | Giacalone . | |
| 4,590,931 | 5/1986 | Kidwell, Jr. . | |
| 4,601,716 | 7/1986 | Smith | 604/349 |
| 4,610,685 | 9/1986 | Raley . | |
| 4,664,104 | 5/1987 | Jaicks . | |
| 4,731,063 | 3/1988 | Newkirk | 602/67 |
| 4,870,958 | 10/1989 | Webster | 602/67 |
| 4,872,462 | 10/1989 | Salz et al. . | |
| 5,036,839 | 8/1991 | Weiss et al. | 602/71 |
| 5,063,915 | 11/1991 | Wychoff . | |
| 5,207,663 | 5/1993 | McQueen | 604/385.1 |
| 5,237,706 | 8/1993 | Nalbandian | 2/403 |

FOREIGN PATENT DOCUMENTS

| | | | |
|---|---|---|---|
| 150429 | 8/1937 | Austria | 604/353 |
| 1115887 | 10/1961 | Germany | 604/351 |
| 3029630 | 3/1982 | Germany | 2/403 |
| 0010406 | of 1914 | United Kingdom | 602/67 |
| 8707136 | 12/1987 | WIPO | 604/349 |
| 9215269 | 9/1992 | WIPO | 604/349 |

*Primary Examiner*—John G. Weiss
*Assistant Examiner*—Karin M. Reichle
*Attorney, Agent, or Firm*—Dykema Gossett PLLC

[57] ABSTRACT

For use in combination with an incontinence garment, a protection device includes a generally planar deflection shield formed of a moisture impervious material. The deflection shield is of sufficient length to extend from above the penis shaft downwardly to the approximate level of the scrotum of the male. The deflection shield includes a clearance aperture permitting the penis shaft to extend through the deflection shield to assure urine is deflected away from the scrotum of the male. The deflection shield includes a sack-like structure extending from a lower portion of the deflection shield adapted to at least partially enclose the scrotum of the male. In an alternative embodiment of the invention, a lower portion of the deflection shield is directly attached to the incontinence garment.

8 Claims, 2 Drawing Sheets

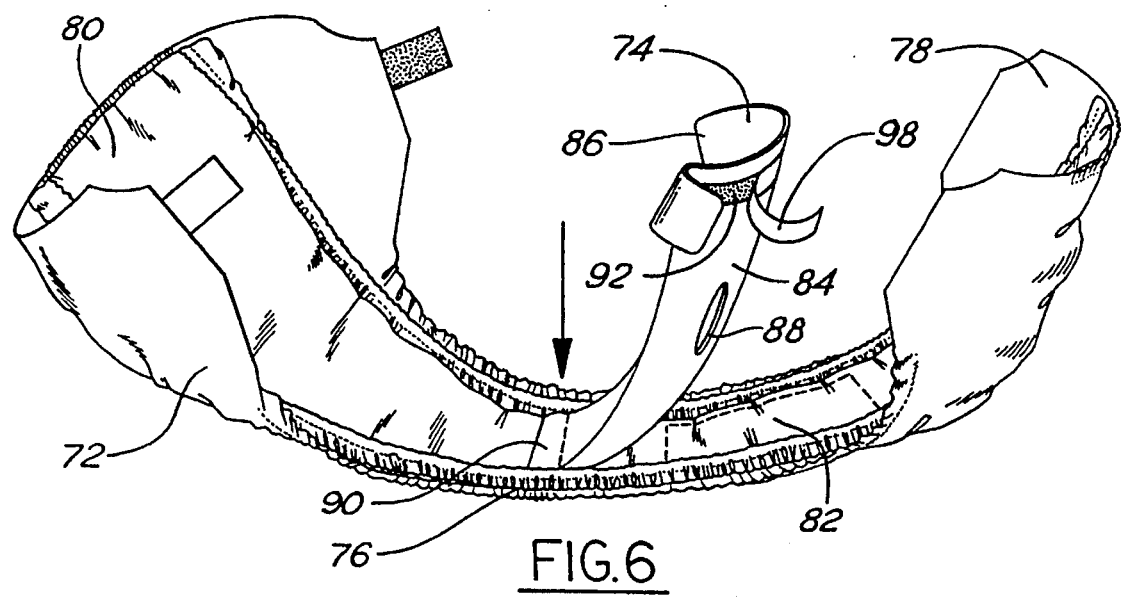
FIG. 6
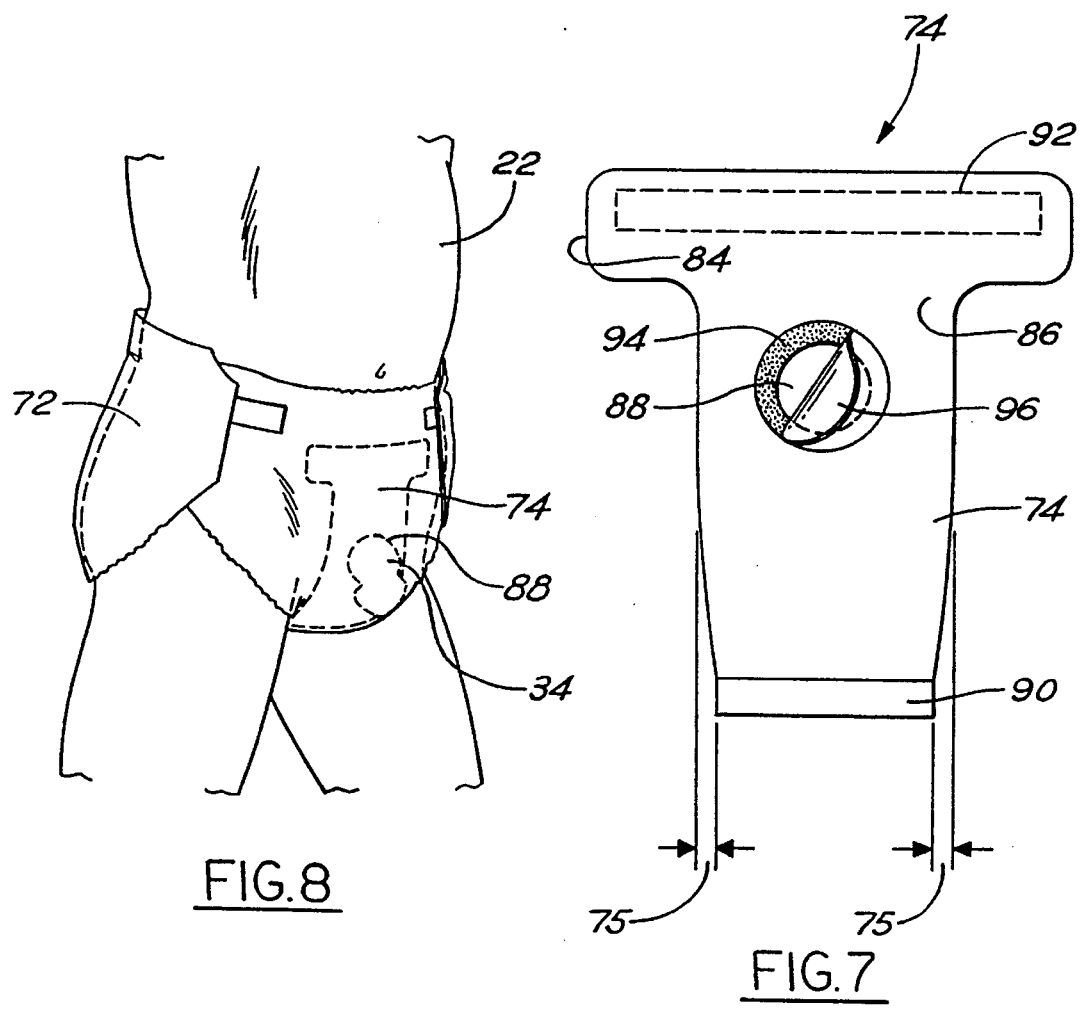
FIG. 8
FIG. 7

MEDICAL PROTECTION DEVICE FOR MALES

This is a continuation of application Ser. No. 08/063,939 filed on May 19, 1993, now abandoned.

BACKGROUND OF THE INVENTION

This invention relates to a medical protection device for males wearing an incontinence garment and, in particular, relates to a deflection shield that provides protection for the scrotum from contact with urine.

The scrotum and perineum (the perineum is the area between the scrotum and anus) are particularly sensitive to periods of prolonged contact with urine or feces. This prolonged contact is problematic for males wearing an incontinence garment, otherwise known as a diaper. Such contact by urine and feces often results in burns, ulceration, skin necrosis and/or secondary infection.

It is well-known in the art to apply lotions and powders to the scrotum and perineum prior to wearing the incontinence garment. Lotions and powders, however, are often washed away by urine and do not provide an adequate solution to the problem. It is also known in the art to enclose the scrotum in a sack-like structure within the incontinence garment itself. These sack-like structures for the scrotum, however, do not properly deflect urine away from the scrotum. In some instances, the prior art structures exaggerate the problem by permitting urine to drip into the sack-like structure. In addition, use of prior art sack-like structures can be cumbersome to attach, uncomfortable to wear, and expensive to produce.

It is therefore an object of the present invention to provide a protection device for the scrotum which is easy to attach, comfortable to wear, and which effectively deflects urine away from the scrotum and perineum. It is a further object of this invention to provide a simple structure that may be used in conjunction with most standard diapers, absorption garments or other incontinence devices.

SUMMARY OF THE INVENTION

The present invention is used in combination with an incontinence garment, and includes a urine deflection shield. The deflection shield is generally planar, and is formed of a moisture impervious material which is pliable. The deflection shield extends from above the penis shaft downwardly to the approximate level of the scrotum of the male. The deflection shield includes a clearance aperture that permits the penis shaft to extend through the deflection shield. In one embodiment of the invention, the deflection shield includes a sack-like structure extending from an end of the deflection shield, which is adapted to at least partially receive the scrotum of the male. In an alternative embodiment of the invention, a lower edge of the deflection shield is directly attached to the perineal portion of the incontinence garment. The deflection shield is adapted to deflect urine away from the scrotum and into an absorption area within the incontinence garment.

BRIEF DESCRIPTION OF THE DRAWINGS

Various features of the present invention will become more apparent upon reading the following detailed description of the preferred embodiments, along with the appended claims in conjunction with the accompanying drawings, wherein identical reference numerals identify like features, and:

FIG. 6 is a fifth embodiment of the protection device shown incorporated into an incontinence garment;

FIG. 7 is a planar view of the embodiment of FIG. 6; and

FIG. 8 is a perspective view of the embodiment of FIG. 6 as worn by a male.

DETAILED DESCRIPTION OF THE PREFERRED EMBODIMENT

Figure 1:
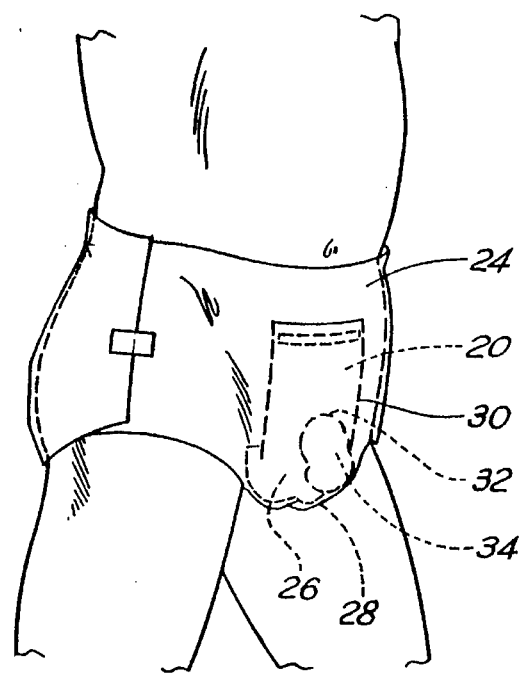
FIG. 1 is a perspective view of an incontinence garment incorporating the protection device of the present invention.

A protection device 20 is shown in FIG. 1 as worn by a male 22 in combination with an incontinence garment 24, more commonly known as a diaper. Incontinence garment 24 is generally worn by those who involuntarily discharge their urine. This problem is common among infants, the elderly, males who have recently undergone prostate surgery, etc.

Protection device 20 is worn to protect the scrotum 26 and perineum from urine. Protection device 20 is placed on the male 22 prior to placement of garment 24. Protection device 20 includes a scrotum guard 28, which is a sack-like structure adapted to partially enclose scrotum 26, and a deflection shield 30, which serves to deflect urine away from scrotum 26. Deflection shield 30 further includes a clearance aperture 32 permitting the penis shaft 34 of the male 22 to protrude through deflection shield 30. A planar portion of deflection shield 30 extends above clearance aperture 32. Clearance aperture 32 in combination with deflection shield 30 assures that urine discharged from male 22 is deflected away from scrotum 26. Further, deflection shield 30 prevents any urine from entering the interior of scrotum guard 28.

Figure 2:
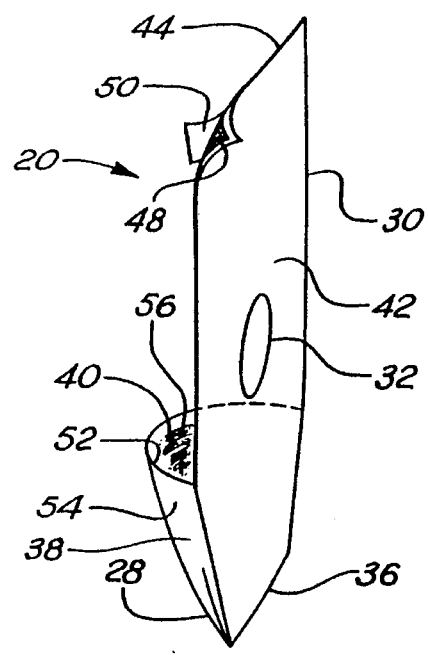
FIG. 2 is an enlarged perspective view of a first embodiment of the protection device.

Referring now to FIG. 2, scrotum guard 28 includes a bottom 36 and a plurality of side walls 38 extending upwardly from bottom 36 to form a sack structure. Scrotum guard 28 includes an opening 40 of sufficient size to hold scrotum 26, as shown in FIG. 1. Deflection shield 30 is integrally attached to scrotum guard 28, and extends upwardly away from one of the side walls 38 a sufficient distance to extend beyond the penis shaft 34. Deflection shield 30 includes a urine deflecting face 42 and a contact face 44. Contact face 44 is oriented to be in direct contact with the skin of male 22. Deflection shield 30 includes an attachment strip 48 on contact face 44 above clearance aperture 32. Attachment strip 48 preferably includes an adhesive surface that facilitates direct attachment of protection device 20 to the abdomen area of male 22. A backing member 50 covers attachment strip 48 prior to use.

Scrotum guard 28 includes an interior surface 52 in direct contact with scrotum 26, and an exterior surface 54 opposing interior surface 52. In the same way that deflecting face 42 acts to keep urine from the scrotum, scrotum guard 28 also deflects urine. Medicating material 56, such as lotion or powder, may be added directly to scrotum 26, or applied to interior surface 52 of scrotum guard 28 prior to placement on male 22. Interior surface 52 therefore serves to continuously coat scrotum 26 with medicating material 56, while exterior surface 54 serves to shield the scrotum 26 from the flow of urine, which may otherwise remove medicating material 56.

Figure 3:
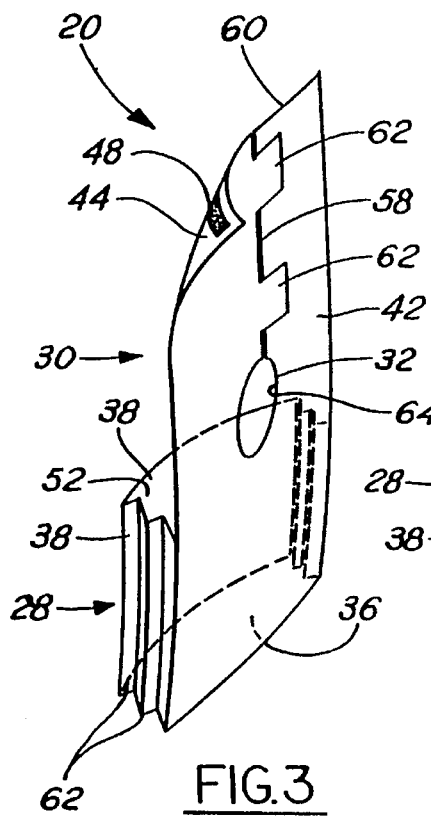
FIG. 3 is a perspective view of a second embodiment of the protection device.
Figure 4:
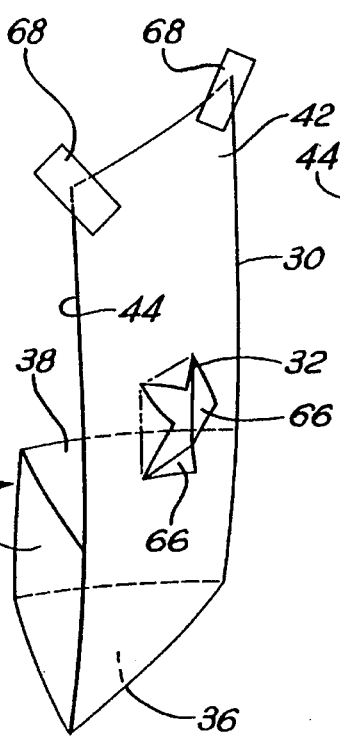
FIG. 4 is a perspective view of a third embodiment of the protection device.
Figure 5:
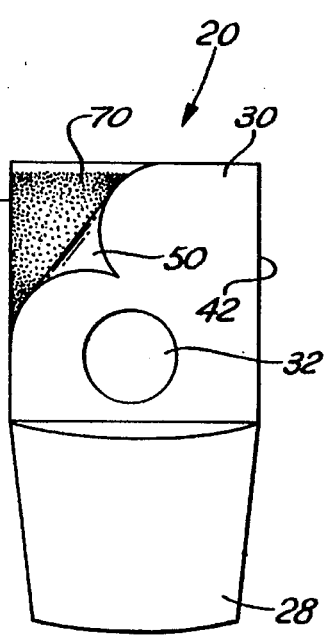
FIG. 5 is a planar view of a fourth embodiment of the protection device.

Alternative embodiments of protection device 20 are illustrated in conjunction with FIGS. 3–5. In FIG. 3, an access slit 58 is shown to extend from clearance aperture 32 upwardly to an upper edge 60 of deflection shield 30. Access slit 58 facilitates placement and removal of protection device 20 by selectively separating portions of deflection shield 30. For example, access slit 58 allows placement and removal of protection device 20 when a catheter (not shown) or similar device is worn by male 22. After protection device 20 is placed on male 22, and deflection shield 30 is properly positioned, access slit 58 may then be closed by surgical tape 62, or similar means.

Bottom 36 of scrotum guard 28 may be rectangular, as in FIG. 3, or triangular as in FIG. 4. A portion of side walls 38 may have a plurality of folds 62 forming a collapsible structure, as shown in FIG. 3. Various other shapes and combinations may also be used without departing from the present invention in order to provide the sack structure having sufficient capacity to hold and partially enclose scrotum 26. These variations of scrotum guard 28 may be used to improve comfort, ease of use, or reduce cost in the manufacturing of protection device 20.

Referring now to FIGS. 3 and 4, clearance aperture 32 may be formed to have several shapes. In FIG. 3, clearance aperture 32 is shown formed as a complete generally circular hole. A disadvantage of the use of a complete hole is that an edge 64 is created. Edge 64 of the hole may scrape the penis shaft 34, causing irritation to the skin. In FIG. 4, clearance aperture 32 is shown formed from a plurality of radial slits. Radial slits are cut to form a plurality of flaps 66 which extend outwardly away from male 22 when penis shaft 38 is placed through deflection shield 30. Use of radial slits eliminates edge 64, thus improving comfort.

Referring now to FIGS. 4 and 5, alternative means of attaching protection device 20 to male 22 are shown. In FIG. 4, attachment of protection device 20 is accomplished by use of surgical tape 68 applied to urine deflecting face 42 of deflection shield 30. In FIG. 5, adhesive area 70 is increased to substantially cover contact face 44 of deflection shield 30. Adhesive area 70 preferably extends below clearance aperture 32 and preferably completely surrounds clearance aperture 32. Adhesive area 70 maintains proper positioning of protection device 20 even under conditions when movement of male 22 is extensive.

Protection device 20 is formed of a moisture impervious material. Further, protection device 20 is pliable and flexible for increased comfort. Preferably, contact face 44 is formed of soft material (i.e. cloth or paper) to reduce irritation and absorb perspiration. Interior surface 52 may also be formed of a soft material, or may be formed of a non-absorbent material to assist in continuously coating scrotum 26 with medicating material 56.

FIG. 6 illustrates an alternative embodiment of the present invention, in which an incontinence garment 72 is shown to include a deflection shield 74. A perineal portion 76 of garment 72 is drawn up between the legs of male 22. Garment 72 includes an anterior flap 78 extending forward with respect to male 22 from perineal portion 76, and a posterior flap 80 extending rearward. When garment 72 is worn, anterior flap 78 provides a urine absorption area 82 in proximity to penis shaft 34.

Deflection shield 74 is directly attached to perineal portion 76 of garment 72. The T-shaped deflection shield 74 includes a urine deflecting face 84 and a contact face 86, such that contact face 86 is in direct contact with the skin of male 22. Deflection shield 74 essentially provides the same function of deflecting urine as previously described for deflection shield 30. Further, deflection shield 74 provides the function of isolating urine into a distinct compartment when garment 72 is worn. Urine is thereby prevented from flowing posteriorly beyond deflection shield 74, protecting the scrotum and buttocks. This embodiment provides the additional advantage of preventing diaper rash caused by urine in the buttocks area.

Referring now to FIG. 7, deflection shield 74 includes a clearance aperture 88 for protrusion of penis shaft 34. A lower portion of deflection shield 74 is preferably permanently attached to perineal portion 76 of garment 72. The attachment may be achieved by any suitable means such as sewing or fusion. Deflection shield 74 is tapered 75 to become narrower towards perineal portion 76 of garment 72. An upper portion of deflection shield 74 includes an upper attachment strip 92 on urine deflection face 84. Upper attachment strip 92 is adapted to be applied to garment 72 when garment 72 is worn. A circular adhesive area 94 is provided concentrically around clearance aperture 88. Backing member 96 covers adhesive area 94 prior to use.

Adhesive area 94 prevents penis shaft 38 from involuntarily withdrawal from clearance aperture 88, and is advantageous when placing garment 74 having deflection shield 74 on a baby. With the exception of adhesive area 94, no adhesive contacts the skin of male 22 with this alternative embodiment.

Clearance aperture 88 may also be formed from radial slits, as previously described. Further, an access slit extending from clearance aperture 88 to an edge of deflection shield 74 may be required if male is wearing a catheter.

FIG. 8 illustrates garment 72 having deflection shield 74 as worn by male 22. Preferably, deflection shield 74 is formed of moisture impervious material, such as thin gauge plastic, and lined with absorbent paper where contacting the skin.

In operation, garment 72 having deflection shield 74 is opened, and then drawn between legs of male 22. Backing member 96 is removed from circular adhesive area 94 and penis shaft 34 is passed through clearance aperture 88. After a backing member 98 is removed from upper attachment strip 92, garment 72 is placed on male 22 in the usual manner. Slight pressure is applied on the exterior of garment 72 to assure attachment of upper attachment strip 92. Deflection shield 74 thereby creates a separate urine chamber and deflects urine away from scrotum 26 towards urine absorption area 82 of garment 72.

Preferred embodiments of the present invention have been described, however, it is to be understood that variations and modifications may be employed without departing from scope of the present invention. The scope of the invention should be determined by reference to the following claims.

I claim:

1. A male protection kit comprising:

an incontinence garment adapted to be drawn between a pair of legs of a male, said incontinence garment including an anterior portion and an a posterior portion, said incontinence garment being adapted for the absorption of bodily fluids; and a shield member formed of a moisture impervious material, said shield member being directly unattached to said incontinence garment but otherwise adapted to be worn by the male with said incontinence garment, said shield member adapted to be positioned between the male and said incontinence garment, said shield member adapted to be coextensive only with said anterior portion of said incontinence garment, said shield member including a clearance aperture adapted for protrusion of a penis shaft of the male through said shield member, said shield member having a first portion and a second portion, said first portion being generally planar and extending substantially above said clearance aperture, said second portion extending below said clearance aperture and including a bottom and a side wall defining a sack structure, said sack structure being adapted for insertion of a scrotum of the male to partially enclose the scrotum within said sack structure, said first portion having an attachment means adapted for directly attaching said shield member only to the male to position said shield member on the male such that said shield member is adapted to be self-supporting on the male, said incontinence garment adapted to overlay said shield member when worn by the male, said shield member adapted to deflect urine towards said incontinence garment.

2. The male protection kit of claim 1, wherein said sack structure of said shield member includes an internal surface area adapted for direct contact with the scrotum of the male, said internal surface including a medicating material.

3. The male protection kit of claim 1, wherein said clearance aperture is formed as a complete hole, said complete hole being of sufficient dimension for protrusion of the penis shaft.

4. The male protection kit of claim 1, wherein said clearance aperture is formed from a plurality of radial slits, said radial slits forming a plurality of flaps allowing for protrusion of the penis shaft.

5. The male protection kit of claim 1, wherein said shield member includes an access slit extending from said clearance aperture to an outer edge of said shield member, said access slit separating portions of said shield member.

6. A protection device for use in combination with an incontinence garment, the incontinence garment adapted to be drawn between a pair of legs of a male and having an anterior portion and a posterior portion, the incontinence garment being adapted for the absorption of bodily fluids, said protection device being directly unattached to said incontinence garment, said protection device comprising:

a generally planar deflection shield formed of a flexible, moisture impervious material, said deflection shield including a clearance aperture adapted for protrusion of a penis shaft of the male through said deflection shield, said deflection shield having an upper portion extending substantially above said clearance aperture, said upper portion of said deflection shield having an attachment means for directly attaching said protection device only to the male, said deflection shield being adapted to be coextensive only with the an anterior portion of the incontinence garment; and a scrotum guard integrally coupled to said deflection shield, said scrotum guard being formed of a flexible, moisture impervious material, said scrotum guard having a bottom portion of a side wall portion defining a sack structure for partially receiving a scrotum of the male.

7. The protection device of claim 6 wherein said sack structure includes an internal surface adapted for direct contact with the scrotum of the male, said internal surface including a medicating material.

8. A protection device for use in combination with an incontinence garment, the incontinence garment adapted to be drawn between a pair of legs of a male and having an anterior portion and a posterior portion, the incontinence garment having an exterior surface and an interior surface, the interior surface being adapted for the absorption of bodily fluids, said protection device being directly unattached to said incontinence garment, said protection device comprising:

a generally planar deflection shield formed of a flexible, moisture impervious material, said deflection shield including a clearance aperture adapted for protrusion of a penis shaft of the male through said deflection shield, said deflection shield having an upper portion extending substantially above said clearance aperture, said upper portion of said deflection shield having an attachment means for directly attaching said protection device only to the male, said deflection shield being adapted to be coextensive with the anterior portion of the incontinence garment; and a scrotum guard integrally coupled to said deflection shield, said scrotum guard being formed of a flexible, moisture impervious material, said scrotum guard having a bottom, a generally planar front wall, and a generally convex rear wall to define a sack structure, said front wall extending from said deflection shield, said rear wall opposing said front wall, wherein said sack structure includes an opening and partially receives and encloses a scrotum thereby partially protecting the scrotum from bodily fluids.

\* \* \* \* \*

UNITED STATES PATENT AND TRADEMARK OFFICE
CERTIFICATE OF CORRECTION

PATENT NO. : 5,618,279
DATED : April 8, 1997
INVENTOR(S) : Pudlo

It is certified that error appears in the above-indentified patent and that said Letters Patent is hereby corrected as shown below:

In column 6, line 6, delete "an".

In column 6, line 11, delete "of" and insert --and--.

In column 6, lines 22-23, delete "having an exterior surface and an interior surface, the interior surface".

Signed and Sealed this

Twenty-fourth Day of June, 1997

Attest:

Attesting Officer

BRUCE LEHMAN

Commissioner of Patents and Trademarks